US00PP14238P39

(12) United States Plant Patent
Bergh et al.

(10) Patent No.: US PP14,238 P3
(45) Date of Patent: Oct. 14, 2003

(54) AVOCADO TREE NAMED 'HARVEST'

(50) Latin Name: *Perssea americana Mill.*
Varietal Denomination: cv. 'N4(-)5'

(75) Inventors: Berthold O. Bergh, Riverside, CA (US); Gray A. Martin, Fallbrook, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/096,581

(22) Filed: Mar. 14, 2002

(65) Prior Publication Data

US 2003/0177555 P1 Sep. 18, 2003

(51) Int. Cl.[7] ..... A01H 5/00

(52) U.S. Cl. ..... Plt./200

(58) Field of Search ..... Plt./200

*Primary Examiner*—Bruce R. Campell
*Assistant Examiner*—Susan B. McCormick
(74) *Attorney, Agent, or Firm*—Burns, Doane, Swecker & Mathis, L.L.P.

(57) ABSTRACT

A new and distinct variety of *Persea americana* tree is provided. An open spreading growth habit is exhibited. The tree exhibits an alternate bearing character similar to that of the widely-grown 'Hass' variety (non-patented in the United States). The fruit is inverted high spheroid-shaped, is generally black-skinned, is well distributed around the tree, and commonly is larger than that of the 'Hass' variety. The leaves are generally oval-shaped. The fruit eating quality is good when fully ripe and the flesh is free of obvious fibers. The variety is suitable for the production of quality avocado crop under commercial growing conditions.

3 Drawing Sheets

Botanical/commercial classification: *Perssea americana* Mill./Avocado Tree.
Varietal denomination: cv. 'N4(-)5'.

SUMMARY OF THE INVENTION

The invention relates to new and distinct variety of Avocado tree that is named 'N4(-)5'.

The seed that produced the new variety of the present invention was collected in 1985 from open-pollinated avocado trees of the 'Gwen' variety U.S. Plant Pat. No. 5,298) growing at Riverside and Irvine, Calif. The exact pollen parent is unknown. Seeds were planted in a test planting area at Ventura County, Calif. to produce avocado seedings in the spring of 1986. The resulting seedling plants were observed and studied and a single plant of the new variety was discovered. Had the new variety not been discovered and carefully preserved it would have been lost to mankind. During about 1992 at the Southcoast Research and Extension Center of the University of California located at Irvine, Calif., the new variety was first top worked by grafting on *Persea americana* seedlings. This and subsequent asexual propagation has confirmed that the new variety is stable and that the progeny are formed true to type.

It was found that the new variety of the present invention exhibits the following combination of characteristics:

(a) exhibits an open spreading growth habit, (b) exhibits an alternate bearing character similar to that of the 'Hass' variety, (c) forms inverted high spheroid-shaped generally black-skinned fruit that is well distributed around the tree which is larger than that of the 'Hass' variety, matures later than the fruit of the 'Hass' variety, and has yellow-green flesh of good eating quality when fully ripe that is free of obvious fibers, and (d) forms generally oval-shaped leaves.

The new 'N4(-)5' variety can be distinguished from all previously known avocado varieties including the 'Hass' variety, the 'Gwen' variety, the 'Sir Prize' variety U.S. Plant Pat. No. 9,709), the 'Lamb Hass' variety U.S. Plant Pat. No. 9,753), and the '3-29-5' variety (U.S. Plant patent application No. 10/096,658, filed Mar. 14, 2002) in view of its distinctive combination of characteristics.

The new 'N4(-)5' variety is believed to be well suited for the production of quality avocados under commercial growing conditions.

BRIEF DESCRIPTION OF THE PHOTOGRAPHS

The accompanying photographs show specimens of the tree and plant parts of the new 'N4(-)5' variety. The trees had been grafted on seedling *Persea americana* understock.

DETAILED DESCRIPTION

Figure 1:
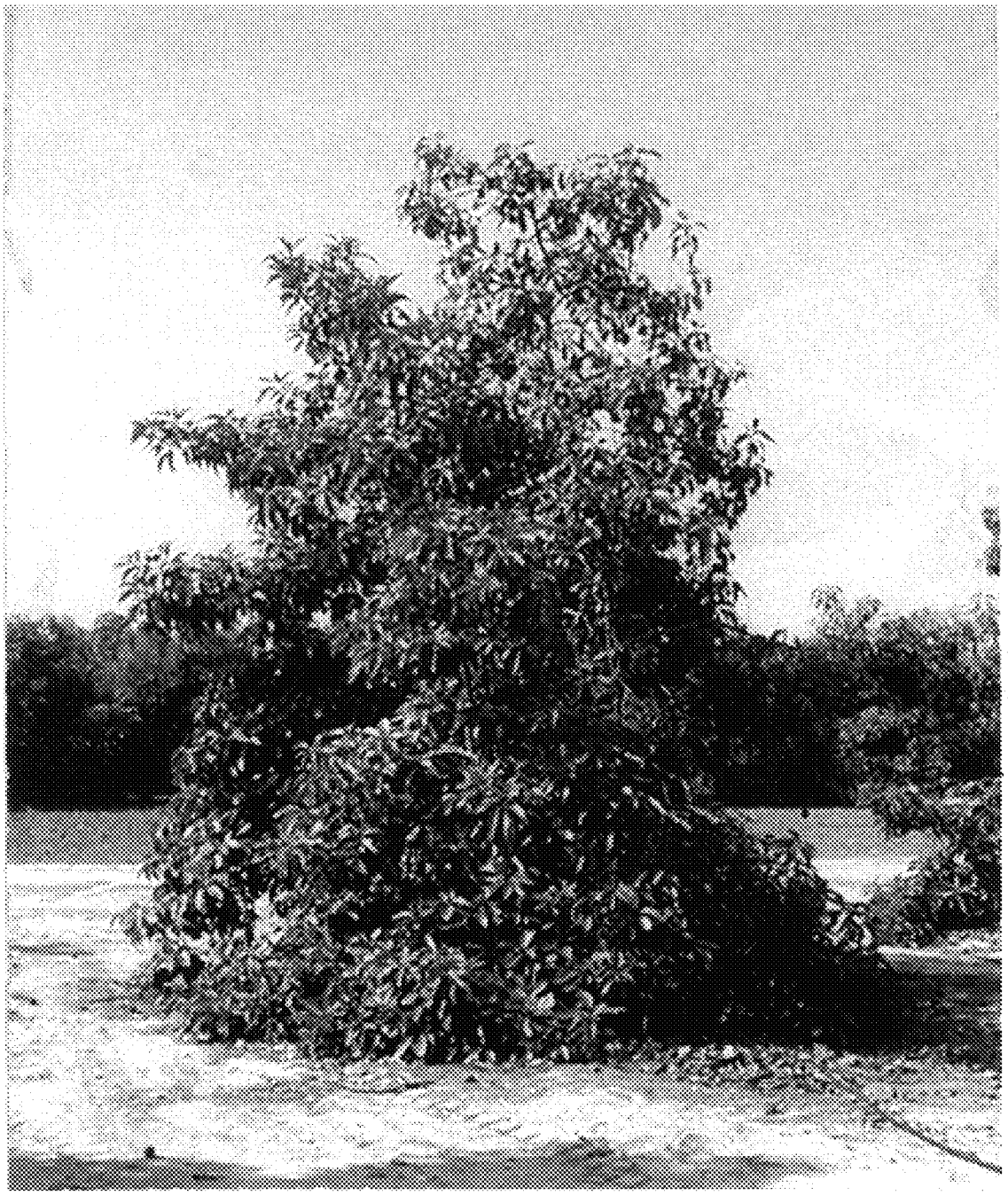
FIG. 1 illustrates a typical six year-old tree of the 'N4(-)5' variety while growing at Irvine, Calif. The open spreading growth habit is shown.
Figure 2:
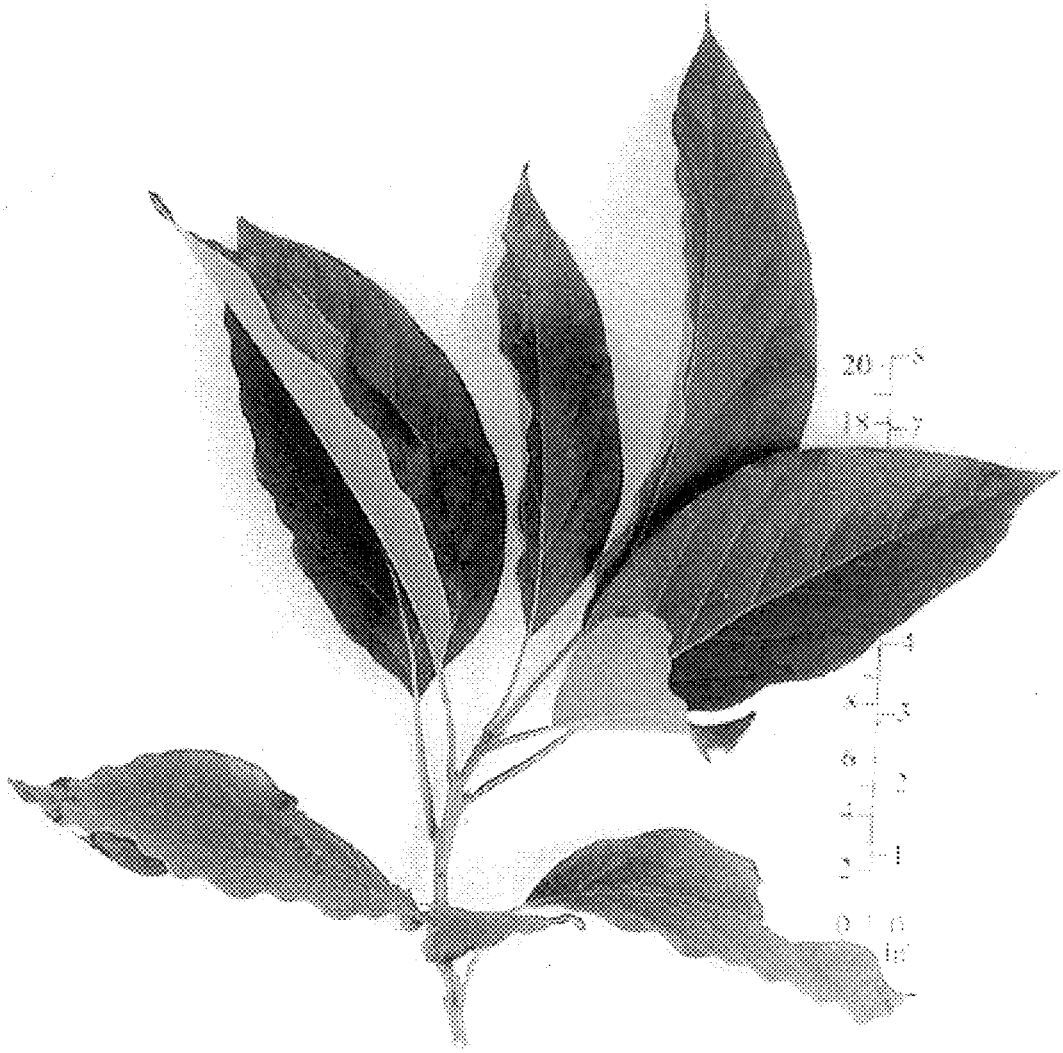
FIG. 2 illustrates typical foliage of the 'N4(-)5' variety as displayed during the summer. Dimensions in centimeters and inches are shown at the right.

The following is a detailed description of the new 'N4(-)5 ' variety. The trees were being grown at experimental orchards of the University of California located at Irvine, Calif., were approximately six years of age, and had been grafted on *Persea americana* seedling understock. When reference to other varieties appears for comparative purposes, such varieties were approximately six years of age with the possible exception of the 'Gwen' variety. The comparative trees of 'Gwen' variety were mature and their exact age was unknown. Color chart information is with reference to The R.H.S. Colour Chart of The Royal Horticultural Society, London, England.

Tree:

*Growth habit.*—Open and spreading. This can be compared to spreading for the 'Hass' variety, moderately-spreading for the 'Gwen' variety, and upright and moderately-spreading for the '3-29-5' variety.

*Height.*—Approximately 4.8 m on average. This can be compared to an average height of 4.6 m for the 'Hass' variety, 3.5 m for the 'Gwen' variety, and 1.5 m for the '3-29-5' variety.

*Width.*—Approximately 4.0 m on average. This can be compared to an average width of 4.3 m for the 'Hass' variety, 3.3 m for the 'Gwen' variety, and 3.5 m for the '3-29-5' variety.

*Bark.*—Substantially identical to that the 'Hass', 'Gwen', and '3-29-5' varieties. The new wood is smooth without corky or specially pigmented lenticels. The old wood is corky in appearance as most other avocado varieties and Greyed-Green Group 196A in coloration.

*Trunk size.*—Approximately 64.5 cm in circumference on average. This can be compared to an average circumference of 57.6 cm for the 'Hass' variety, 38.9 cm for the 'Gwen' variety, and 51.0 cm for the '3-29-35' variety.

Leaves:

*Shape.*—Generally oval with an acute tip and an acute base. The shape is substantially the same as that of the 'Hass' and 'Gwen' varieties. This can be compared to lanceolate with an acute tip and an acute base for the '3-29-5' variety.

*Bearing.*—Alternate.

*Length.*—Approximately 15.4 cm on average. This can be compared to 18.0 cm for the 'Hass' variety, 16.0 cm for the 'Gwen' variety, and 15.4 cm for the '3-29-5' variety on average.

*Width.*—Approximately 6.5 cm on average. This can be compared to 6.4 cm for the 'Hass' variety, approximately 5.6 cm for the 'Gwen' variety, and approximately 5.9 cm for the '3-29-5' variety on average.

*Leaf weight.*—Approximately 2.17 g on average. This can be compared to approximately 2.67 g for the 'Hass' variety, approximately 1.73 g for the 'Gwen' variety, and approximately 1.78 g for the '3-29-5' variety on average.

*Color.*—Near Green Group 139A on the upper surface and near Green Group 137C on the under surface.

*Texture.*—Pubescent when young and becoming smooth and leathery when mature.

*Venation.*—Pinnate and near Green Group 146D in coloration.

*Margin.*—Entire and slightly wavy.

*Petiole.*—Commonly approximately 41.9 mm in length, and approximately 2.5 mm in diameter.

Flowers:

*Type.*—Synchronous dichogamy, and borne in panicles.

*Bud size.*—Approximately 8.3 mm in length and approximately 3 mm in diameter.

*Bud shape.*—Lanceolate to oblong-lanceolate.

*Bud color.*—Commonly near yellow-green group 151A.

*Opening.*—Open as female on the morning of the first day, and close in late morning or early afternoon. Such flowers generally remain closed until the afternoon of the second day when they open as male. Such opening sequence commonly is designated as being the "Type A". This flowering behavior is believed to promote cross-pollination since the male and female phases of an individual flower occur at different times. Accordingly, the interplanting of complementary flower types possibly boosts fruit set and yield by making pollen available at the appropriate time. Bees (e.g., European honey bees) can be used to advantage as pollinators.

*Petals.*—Borne in two whorls of three perianth lobes. The petals are more or less pubescent, the margins are entire, and the petal color is near yellow-green group 151A.

*Stamen.*—There commonly are nine fertile stamens with each having four pollen chambers, two basal orange nectar glands, and three staminodia. The anthers are tetrathecal.

*Pistil.*—The single pistil has one carpel with one ovule.

*Pedicel.*—Commonly approximately 7.8 mm in length and approximately 0.6 mm in diameter. The coloration is near yellow-green group 151A.

Fruit:

*Pick dates.*—Commonly fall into early winter. This compares to February to July or August for the 'Hass' variety, late February or March into June for the 'Gwen' variety, and March to July for the '3-29-5' variety.

*Bearing.*—Alternate bearing similar to the 'Hass' variety. The fruit is well distributed around the tree and tends to be protected inside the leaf canopy.

*Shape.*—Inverted high spheroid. The 'Hass' fruit configuration has been found to vary from ellipsoid to obovate from year to year. The 'Gwen' and '3-29-5' fruit configuration is generally inverted high spheroid.

*Base.*—Inflated.

*Apex.*—Rounded.

*Size.*—Generally larger than that of the 'Haas' variety. An average fruit weight was found to be 232 g. This can be compared to 204 g for the 'Hass' variety, 210 g for the 'Gwen' variety, and 235 g for the '3-29-5' variety. The fruit commonly is approximately 87 mm in length and approximately 71 mm in diameter.

Figure 3:
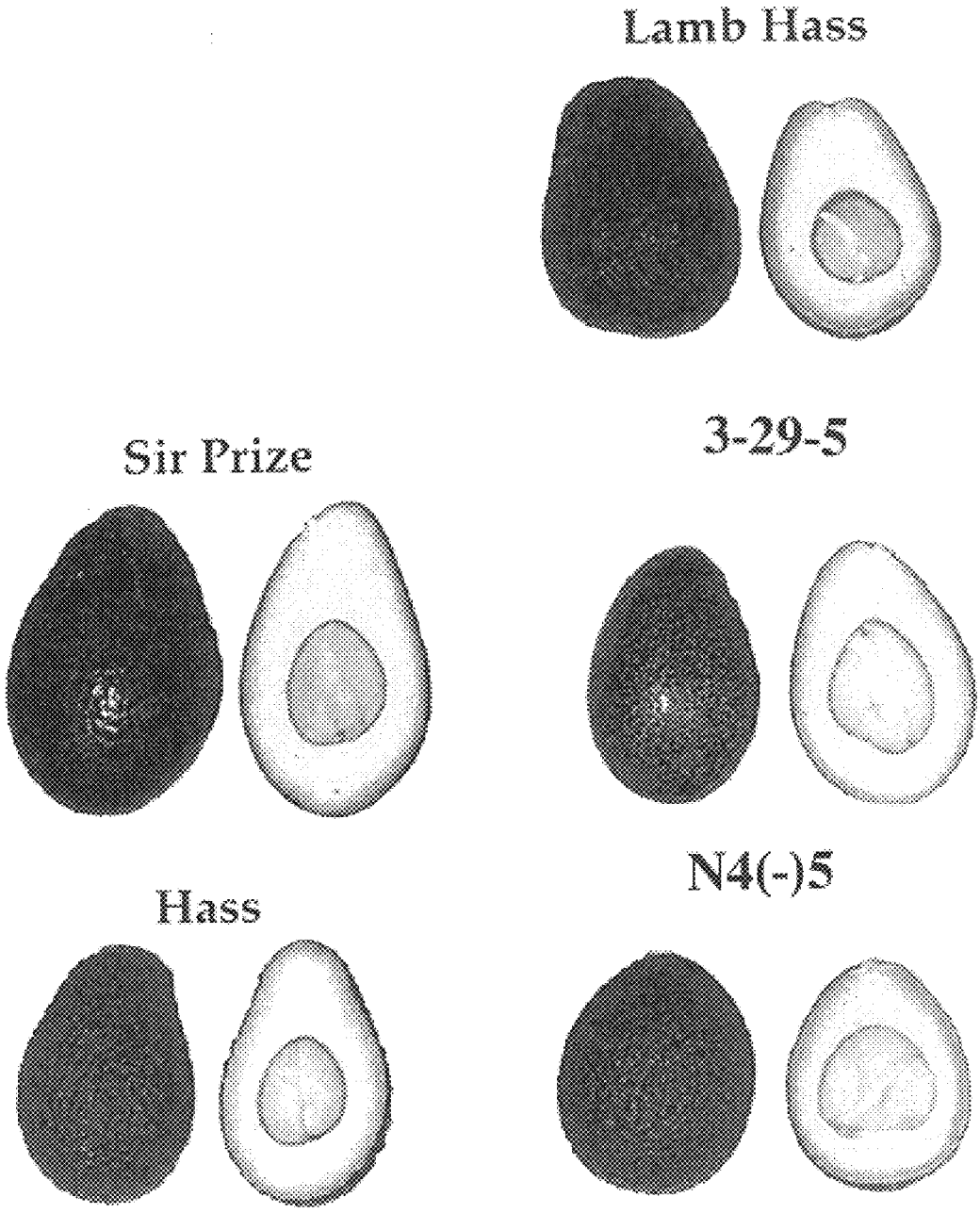
FIG. 3 illustrates typical external and internal views of the fruit of the 'N4(-)5' variety at the lower right. For comparative purposes the fruit of the 'Sir Prize', 'Hass', 'Lamb Hass' and '3-29-5' varieties also is included.

*Skin color.*—Very attractive and generally black when soft with numerous light yellow-green lenticels (as illustrated in FIG. 3). With reference to The R.H.S. Colour Chart the skin commonly is near green group 137A to 137when hard, and purple group 79A to black when soft.

*Flesh color.*—Yellow-green (near yellow green group 153C) with more green towards the skin.

*Texture.*—Slightly pebbled. The environment has been found to influence the roughness of the skin surface.

*Percent dry weight.*—This is an indirect measure of the oil content of the avocado fruit. 22.35 percent dry matter on average with a maximum of 27.21 percent on Oct. 24, 2001. This compares to 28.77 percent dry matter on average for 'Haas' with a maximum of 35.01 percent on Jul. 23, 2001, and 29.48 percent dry matter on average for '3-29-5' with a maximum of 36.17 percent on Sep. 4, 2001.

*Skin character.*—Pliable.

*Skin thickness.*—Approximately 1.7 mm on average. This can be compared to 1.6 mm for the 'Hass' variety, 1.3 mm for the 'Gwen' variety, and 1.6 mm for the '3-29-5' variety on average.

*Skin separation.*—Separates readily and cleanly from the flesh when ripe.

*Seed/skin/flesh ratio by weight.*—Approximately 19:16:65. This can be compared to 14:13:73 for the 'Hass' variety, 18:13:69 for the 'Gwen' variety, and 18:13:69 for the '3-29-5' variety.

*Flavor.*—Eating quality is good when fully ripe. When immature, exhibits a bittersweet taste. The flavor of the 'Gwen' fruit also is generally comparable to that of the 'Hass' variety and is considered to be slightly better by some. The flavor of the '3-29-5' variety is excellent and is similar to that of the 'Hass' variety. Also, the flavor of the '3-29-5' variety is slightly less nutty than the 'Hass' variety and possesses a buttery texture.

*Fruit fibers.*—No obvious fruit fibers are apparent.

*Seed shape.*—Spheroid. This compares to variable mostly ellipsoid for the 'Hass' variety, spheroid for the 'Gwen' variety, and broadly ovate for the '3-29-5' variety.

*Seed weight.*—Approximately 41.2 g on average. This compares to 28.4 g for the 'Hass' variety, 38.8 g for the 'Gwen' variety, and 36.0 g for the '3-29-5' variety on average.

*Seed size.*—Commonly approximately 40.7 mm in diameter (longest dimension).

*Seed coat.*—Commonly near greyed-orange group 166B in coloration.

*Cotyledon.*—Commonly near orange-white group 159C in coloration.

Productivity: Observations to date indicate a greater productivity than that of the 'Hass' variety.

Hardiness: Generally comparable to that of the 'Gwen' variety, and somewhat less hardy than the 'Hass' and '3-29-5' varieties.

Market use: The fruit is well suited for the fresh retail and food service markets. Also, the fruit can serve as a source for processed guacamole and other avocado by-products.

We claim:

1. A new and distinct variety of *Persea americana* plant having the following combination of characteristics:

(a) exhibits an open spreading growth habit, (b) exhibits an alternate bearing character similar to that of the 'Hass' variety, (c) forms inverted high spheroid-shaped generally black-skinned fruit that is well distributed around the tree which commonly is larger than that of the 'Hass' variety, matures later than the fruit of the 'Hass' variety, and has yellow-green flesh of good eating quality when fully ripe that is free of obvious fibers, and (d) forms generally oval-shaped leaves;

substantially as illustrated and described.

* * * * *

UNITED STATES PATENT AND TRADEMARK OFFICE

CERTIFICATE OF CORRECTION

PATENT NO. : PP 14,238 P3
DATED : October 14, 2003
INVENTOR(S) : Berthold O. Bergh et al.

It is certified that error appears in the above-identified patent and that said Letters Patent is hereby corrected as shown below:

Title page,
Item [54], Title, delete "AVOCADO TREE NAMED 'HARVEST'" and insert -- AVOCADO TREE NAMED 'N4(-)5' --.

Signed and Sealed this

Tenth Day of February, 2004

JON W. DUDAS
*Acting Director of the United States Patent and Trademark Office*